US00PP10317P

United States Patent [19]

Shimizu

[11] Patent Number: Plant 10,317

[45] Date of Patent: Apr. 7, 1998

[54] *LONICERA JAPONICA* 'HINLON'

[75] Inventor: Toshiro Shimizu, Yamaguchi Prefecture, Japan

[73] Assignee: Hines Horticulture, Inc., Irvine, Calif.

[21] Appl. No.: 759,605

[22] Filed: Dec. 5, 1996

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—Christie, Parker & Hale, LLP

[57] ABSTRACT

A new plant variety of *Lonicera japonica* having yellow-margined variegated foliage.

2 Drawing Sheets

BACKGROUND OF THE INVENTION

The present invention relates to a new and distinct variety of *Lonicera japonica* and was discovered as a branch sport in a controlled planting of *Lonicera japonica* in Kuga-Cho, Kuga-Gun, Yamaguchi Prefecture, Japan. The varietal denomination of the new variety is 'Hinlon'.

The genus Lonicera is included in the family Caprifoliaceae which comprises about 15 genera of shrubs growing in the northern and southern hemispheres. Lonicera comprises over 200 species of deciduous or evergreen shrubs, many of which possess desirable ornamental characteristics. *Lonicera japonica* is widespread and common throughout much of Japan, Korea and China. It generally has opposite, oval to rounded leaves 3 to 7 cm. long and 1 to 3 cm. wide. The leaves on vigorous young shoots are sometimes lobed. The plant is deciduous or partly-to-fully evergreen depending on winter temperature. Leaf color ranges from light to dark green, depending on light intensity and cultural conditions. Young shoots are sometimes purplish under cool growing conditions. Leaves are generally softly pubescent overall, but sometimes nearly or completely hairless, especially on top. Some botanists separate those plants with little hair under the variety designation *L. repens* Rehder.

Flowers of *Lonicera japonica* are borne in pairs in the leaf axils and are tubular, 3 to 4 cm. long, and divided and flared at the end. Flower color is white at first, ageing to pale yellow and the flowers are sweetly fragrant, more so at night. Flowering begins in early summer, and continues through the rest of the growing season. *Lonicera japonica* in several forms is believed to have been cultivated in Europe and North America for about 200 years, but only one cultivar with colored (variegated) foliage is known to have been grown outside Asia. This variety is known as cv. 'Aureoreticulata' and was introduced to England from Asia in about 1862.

SUMMARY OF THE INVENTION

The new variety was discovered as a branch sport in a controlled planting of *Lonicera japonica* and differs from its parent in having yellow-margined variegated foliage. Asexual reproduction of the new variety by stem cuttings performed in Yamaguchi Prefecture, Japan; Lewisberry, Pa.; Vacaville, Calif.; and Fulshear, Tex.; have confirmed that the distinctive characteristics of the new variety are stable and transmitted to succeeding generations.

BRIEF DESCRIPTION OF THE ILLUSTRATIONS

The accompanying illustrations show specimens of the new cultivar in a photo illustration as true to color as is reasonably possible to make in an illustration of this character.

In the illustrations:

FIG. 1 shows typical foliage of the parent *Lonicera japonica* as grown in the United States;

FIG. 2 illustrates the foliage of the new variety and shows the distinctive pattern of variegation as well as the glossy leaf surface, the slightly undulate margin and the reddish-brown stem coloration; and FIG. 3 is an illustration of the foliage of the only other known variegated variety of *Lonicera japonica* believed to be grown in the United States, cv. 'Aureoreticulata' which has a reticulate variegation pattern, following the pattern of venation, and not marginal.

COMPARISON WITH THE PARENT

The new variety differs from its parent in having yellow to yellow-green leaf margins about 1 to 5 mm. wide, instead of entirely green leaves.

DETAILED DESCRIPTION OF THE NEW VARIETY

Figure 1:
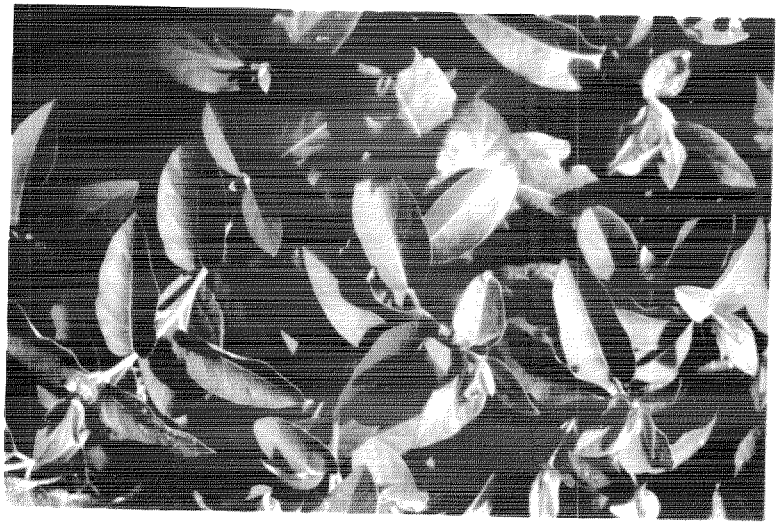
Figure 2:
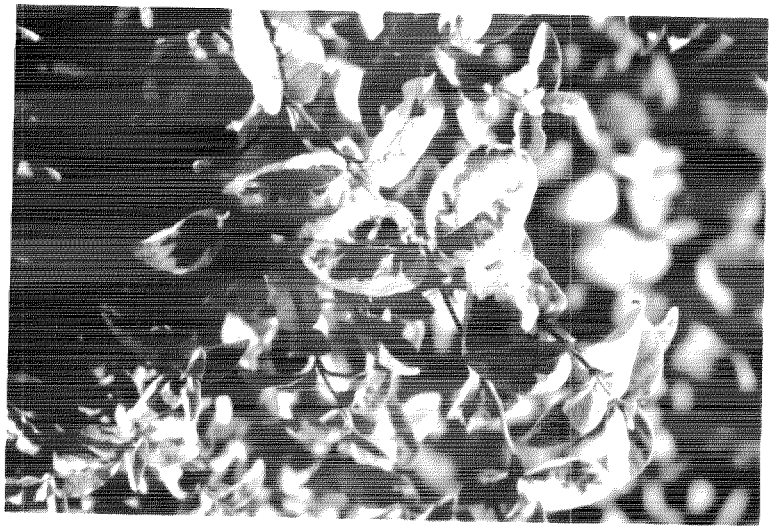
Figure 3:
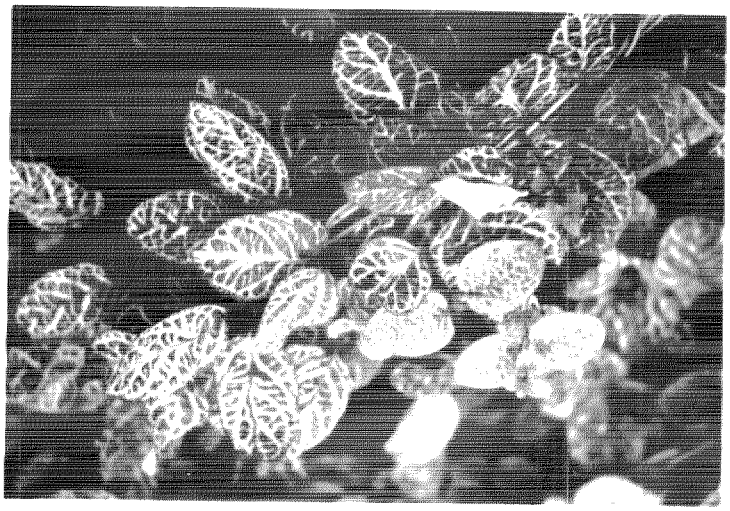

'Hinlon' has not been observed under all possible environmental, cultural, and light conditions. The following observations and descriptions are of plants grown in containers at Lewisberry, Pa., and Vacaville, Calif. In this description, color references are to The Royal Horticultural Society Colour Chart and terminology used in the color descriptions herein refers to plate numbers in this color chart. Phenotypic expression may vary with light intensity, cultural, and environmental conditions.

Classification:

*Botanical*—. *Lonicera japonica* cv. 'Hinlon'.

*Parentage*.—Branch sport of the variety '*Lonicera japonica*'.

*Propagation*.—By vegetative cuttings and other known asexual reproduction techniques.

Plant:

*Size*.—Mature plant can climb and spread to about 10 meters at maturity.

*Habit*.—A scrambling, twining vine that can be grown on the ground, or allowed to climb screens or trellises.

*Leaves*.—Simple, entire, opposite on stems, near 176B. Leaf margin: Smooth, often slightly undulate, with curved hairs.

*Color of mature leaves*.—Leaf top surface: Color varies with intensity of sunlight and cultural conditions (see below). Color readings from four different conditions in August: Lewisberry, Pa., about 70% shade: Upper surface margin near 144B; upper surface center near 139A. Vacaville, Ca., no shade: Upper surface margin near 150B; upper surface center near green group 136A. Vacaville, Ca., about 50% shade: Upper surface margin near 145A; upper surface center near 137A. Vacaville, Ca., about 75% shade: Upper surface margin near 144A; upper surface center near 137A. Leaf undersurface: Somewhat glaucous, near 191B.

*Leaf size.*—Average about 1.5 to 3 cm wide, about 3 to 5 cm long.

*Shape.*—Ovate to nearly elliptic.

*Texture and substance.*—Firm, chartaceous to nearly coriaceous, smooth and moderately glossy to glossy above, nearly smooth and glaucous beneath, with a few very sparse, scattered hairs, especially along the leaf margin.

*Leaf apex.*—Occasionally acute, usually obtuse to nearly rounded, apiculate.

*Petioles.*—About 5 mm. long, hairy.

*Hardiness.*—USDA Zone 5 (−20° to −10° F.).

Inflorescence:

*Bloom period.*—Early summer to fall.

*Flower form.*—Tubular, flared and divided at end.

*Flower arrangement.*—Paired in leaf axils, sometimes crowded at tips of branches.

*Flower size.*—About 2.8 to 3.8 cm. long.

*Color.*—White, changing to pale yellow as flowers age; may be tinted purple under cool growing conditions.

*Peduncles.*—Very short (flower almost sessile).

*Fragrance.*—Sweet, intense, strongest at night.

Reproductive system:

*Stamens.*—5.

*Pistils.*—1.

*Fruit.*—Blue-black berry; 6 to 7 mm. wide.

I claim:

1. A new and distinct variety of *Lonicera japonica* plant named 'Hinlon' substantially as illustrated and described, particularly characterized by yellow-margined variegated foliage.

* * * * *